(12) United States Patent
Sharma et al.

(10) Patent No.: US 8,983,809 B2
(45) Date of Patent: Mar. 17, 2015

(54) METHOD AND SYSTEM FOR PATIENT-SPECIFIC HEMODYNAMIC ASSESSMENT OF VIRTUAL STENT IMPLANTATION

(75) Inventors: Puneet Sharma, Rahway, NJ (US); Viorel Mihalef, Keasbey, NJ (US); Razvan Ioan Ionasec, Princeton, NJ (US); Bogdan Georgescu, Plainsboro, NJ (US); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 378 days.

(21) Appl. No.: 13/311,989

(22) Filed: Dec. 6, 2011

(65) Prior Publication Data

US 2013/0144573 A1 Jun. 6, 2013

(51) Int. Cl.
*G06F 17/50* (2006.01)
*G06F 19/00* (2011.01)
*A61F 2/90* (2013.01)

(52) U.S. Cl.
CPC ........ *G06F 19/3437* (2013.01); *G06F 2217/00* (2013.01); *A61F 2/90* (2013.01)
USPC .......................................................... 703/2

(58) Field of Classification Search
CPC .... G06F 2217/00; G06F 19/3437; A61F 2/90
USPC ............................................................. 703/2
See application file for complete search history.

(56) References Cited

U.S. PATENT DOCUMENTS

| | | | |
|---|---|---|---|
| 7,860,290 B2 | 12/2010 | Gulsun et al. | |
| 7,953,266 B2 | 5/2011 | Gulsun et al. | |
| 2002/0068968 A1* | 6/2002 | Hupp ........................... | 623/1.15 |
| 2008/0101676 A1 | 5/2008 | Zheng et al. | |
| 2008/0262814 A1 | 10/2008 | Zheng et al. | |
| 2009/0088830 A1 | 4/2009 | Mohamed et al. | |
| 2009/0123050 A1 | 5/2009 | Ionasec et al. | |
| 2009/0154785 A1* | 6/2009 | Lynch et al. .................. | 382/131 |
| 2010/0067760 A1 | 3/2010 | Zhang et al. | |
| 2010/0070249 A1 | 3/2010 | Ionasec et al. | |
| 2010/0239147 A1 | 9/2010 | Vitanovski et al. | |
| 2010/0239148 A1 | 9/2010 | Zheng et al. | |

(Continued)

OTHER PUBLICATIONS

B.J.B.M. Wolters, M.C.M. Rutten, G.W.H. Schurink, U. Kose, J. de Hart, F.N. van de Vosse, "A patient-specific computational model of fluid-structure interaction in abdominal aortic aneurysms" Medical Engineering & Physics, 2005, pp. 871-883.*

(Continued)

*Primary Examiner* — Dwin M Craig

(57) ABSTRACT

A method and system for assessment of virtual stent implantation in an aortic aneurysm is disclosed. A patient-specific 4D anatomical model of the aorta is generated from the 4D medical imaging data. A model representing mechanical properties of the aorta wall is adjusted to reflect changes due to aneurysm growth at a plurality of time stages. A stable deformation configuration of the aorta is generated for each time stages by performing fluid structure interaction (FSI) simulations using the patient-specific 4D anatomical model at each time stage based on the adjusted model representing the mechanical properties of the aorta wall at each time stage. Virtual stent implantation is performed for each stable deformation configuration of the aorta and FSI simulations are performed for each virtual stent implantation.

27 Claims, 5 Drawing Sheets

(56) References Cited

U.S. PATENT DOCUMENTS

2010/0280352 A1* 11/2010 Ionasec et al. ............... 600/407
2010/0299077 A1* 11/2010 Kassab et al. ................ 702/19
2011/0060576 A1   3/2011 Sharma et al.

OTHER PUBLICATIONS

Zhonghua Sun, Thanapong Chaichana, "Investigation of the Hemodynamic Effect of Stent Wires on Renal Arteries in Patients with Abdominal Aortic Aneurysms Treated with Suprarenal Stent-Grafts" Cardiovasc Intervent Radiol, Mar. 17, 2009, pp. 647-657.*

Christine M. Scotti, Ender A. Finol; "Compliant biomechanics of abdominal aortic aneurysms: A fluid-structure interaction study" 2006 Elsevier Ltd. pp. 1097-1112.*

Yang et al., "3D Ultrasound Tracking of the Left Ventricles Using One-Step Forward Prediction and Data Fusion of Collaborative Trackers", CVPR 2008.

Ionasec et al., "Patient-Specific Modeling and Quantification of the Aortic and Mitral Valves from 4D Cardiac CT and TEE", IEEE Transactions on Medical Imaging, 2010.

Ionasec et al., "Robust Motion Estimation Using Trajectory Spectrum Learning: Application to Aortic and Mitral Valve Modeling from 4D TEE", Proceedings of 12th IEEE International Conference on Computer Vision, 2008, pp. 1601-1608.

S. Mantero, et al., "The Coronary Bed and its Role in the Cardiovascular System: A Review and an Introductory Single-Branch Model", Journal of Biomedical Engineering, vol. 14, Issue 2, Mar. 1992, pp. 109-116.

P.N. Watton, et al., "Evolving Mechanical Properties of a Model of Abdominal Aortic Aneurysm", Biomechanics and Modeling in Mechanobiology, vol. 8, Issue 1, 2007.

* cited by examiner

METHOD AND SYSTEM FOR PATIENT-SPECIFIC HEMODYNAMIC ASSESSMENT OF VIRTUAL STENT IMPLANTATION

BACKGROUND OF THE INVENTION

The present invention relates to modeling the aorta using medical images, and more particularly, to patient-specific hemodynamic assessment of virtual stent implantation in the aorta based on medical images.

An aortic aneurysm is the swelling or dilation of the aorta, typically representing an underlying weakness in the wall of the aorta at a particular location. If untreated, an aortic aneurysm can progressively grow and possibly rupture, which can cause severe internal hemorrhaging often leading to death. Aortic aneurysms may occur anywhere on the aorta, including thoracic aortic aneurysms, abdominal aortic aneurysms, and aortic root aneurysms. Minimally invasive techniques have been used in recent years as an alternative to open surgery. In particular, percutaneous implantation of an endovascular stent at the diseased portion of the aorta is a common technique for treating an aortic aneurysm. In a percutaneous aortic stent implantation, a stent is delivered to the diseased portion of the aorta through a catheter.

BRIEF SUMMARY OF THE INVENTION

The present invention provides a method and system for hemodynamic assessment of virtual stent implantation in the aorta using medical image data. In particular, embodiments of the present invention provide patient-specific hemodynamic assessment of virtual stent implantation in an aorta having a progressively growing aortic aneurysm for treatment planning and decision support.

In one embodiment of the present invention, a patient-specific 4D anatomical model of the aorta is generated from the 4D medical imaging data. A model representing mechanical properties of the aorta wall is adjusted to reflect changes due to aneurysm growth at a plurality of time stages. A stable deformation configuration of the aorta is generated for each time stages by performing fluid structure interaction (FSI) simulations using the patient-specific 4D anatomical model at each time stage based on the adjusted model representing the mechanical properties of the aorta wall at each time stage. Virtual stent implantation is performed for each stable deformation configuration of the aorta and FSI simulations are performed for each virtual stent implantation.

These and other advantages of the invention will be apparent to those of ordinary skill in the art by reference to the following detailed description and the accompanying drawings.

DETAILED DESCRIPTION

The present invention relates to hemodynamic assessment of virtual stent implantation in the aorta using medical image data, such as computed tomography (CT), magnetic resonance imaging (MRI), and echocardiography data. Sequences of volumetric data, referred to herein as 4D image data or 4D images, are sequences taken over a period of time to cover one or more cardiac cycles, in which each frame is a 3D image (volume). Embodiments of the present invention are described herein to give a visual understanding of the virtual stent implantation assessment method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention provide a method and system for hemodynamic assessment of virtual stent implantation in the aorta using medical image data. In particular, embodiments of the present invention provide patient-specific hemodynamic assessment of virtual stent implantation in an aorta having a progressively growing aortic aneurysm for treatment planning and decision support. A patient-specific 4D anatomic model of the aorta is obtained from high-resolution medical images, such as 4D CT images or 4D MRI images. The growth of an aneurysm over time is simulated by a mathematical model which is based on an underlying realistic structural analysis of the aortic wall. This is followed by virtually implanting a stent in the geometric model of the aorta with the aneurysm and performing Fluid-Structure Interaction (FSI) simulations to obtain hemodynamic parameters for functional assessment of the stent implantation.

Figure 1:
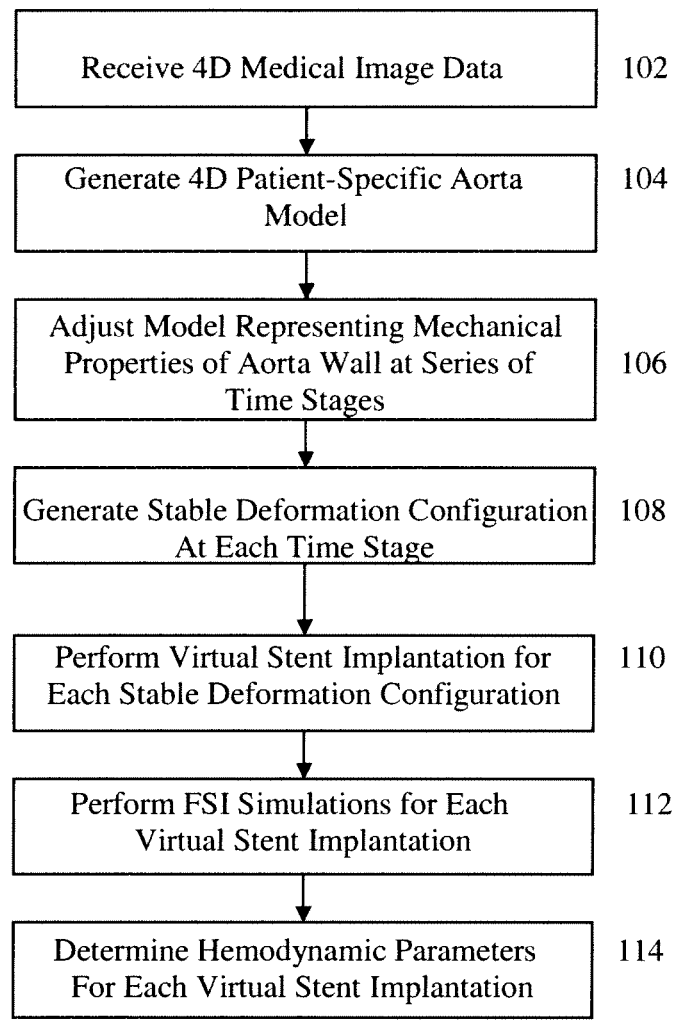
FIG. 1 illustrates a method for hemodynamic assessment of virtual stent implantation in the aorta according to an embodiment of the present invention.

FIG. 1 illustrates a method for hemodynamic assessment of virtual stent implantation in the aorta according to an embodiment of the present invention. Referring to FIG. 1, at step 102, 4D medical image data is received. In particular, at least one sequence of volumetric image data is received. The sequence of volumetric image data can be a sequence of 3D images (volumes) acquired over a certain time period. For example, such a 4D image data (3D+time) can be acquired over at least one full heart cycle. One or more sequences can be received using various medical imaging modalities. For example, according to various embodiments of the present invention, 4D CT data, 4D echocardiography, and/or 4D magnetic resonance (MR) image data can be received, as well as other types of image data. In one embodiment, high resolution CT or MR image data is received. The image data can be received directly from one or more image acquisition devices, such as a CT scanner, an ultrasound device, or an MR scanner. It is also possible that previously stored image data be loaded, for example from a memory or storage of a computer system or some other computer readable storage medium.

Figure 2:
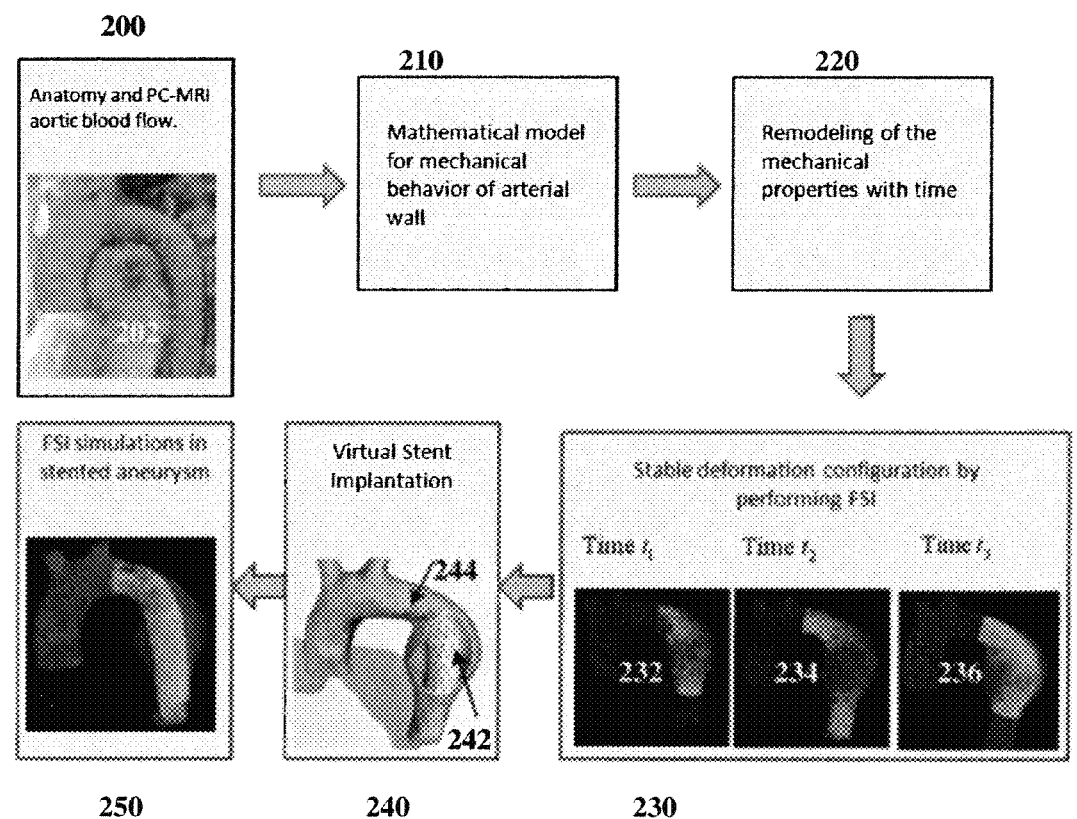
FIG. 2 is a block diagram illustrating the method steps of FIG. 1.

At step 104, a 4D patient specific aorta model is generated from the 4D image data. In particular, a patient specific anatomic model of the aorta is generated in addition to 4D blood flow measurements in the aorta. The patient specific anatomic model of the aorta may be generated in each frame of the 4D image data using the piece-wise aorta segmentation method described in United States Published Patent Application No. 2010/0239148, the disclosure of which is incorporated herein by reference. The patient specific anatomical model of the aorta may be generated as part of a patient specific 4D anatomical model of the entire heart, for example using the methods described in U.S. patent application Ser. No. 13/091, 076, entitled "Method and System for Comprehensive Patient-Specific Modeling of the Heart", filed Apr. 20, 2011, the disclosure of which is incorporated herein by reference. In one embodiment, the aortic blood flow measurements can be generated using phase contrast magnetic resonance imaging (PC-MRI) data. FIG. 2 is a block diagram illustrating the method steps of FIG. 1. As shown in FIG. 2, block 200 shows exemplary results of generating a patient-specific model of the aorta. As shown in block 200, a patient specific aorta model 202 shows the anatomy of the aorta, as well as the PC-MRI aortic blood flow.

Returning to FIG. 1, at step 106, a model representing mechanical properties of the aorta wall is adjusted to reflect changes due to aneurysm growth at a series of discrete time steps. The mechanical behavior of the aorta wall can be characterized by a mathematical model (block 210 of FIG. 2). In an advantageous embodiment, the mechanical behavior of the aorta wall is characterized using a mathematical model which is based on an underlying realistic structural analysis of the three layers of the aortic wall under internal pressure, as described in P. N. Watton et al., "Evolving Mechanical Properties of a Model of Abdominal Aortic Aneurysm," *Biomechanics and Modeling in Mechanobiology*, Vol. 8, Issue 1, 2007, which is incorporated herein by reference. At a first time stage, parameters of the model are set based on the geometric properties derived from the patient-specific anatomical model of the aorta. The size of the aortic aneurysm at the current time is known based on the patient-specific anatomical model and the aneurysm progressively grows with time. This growth can be simulated based on the mechanical properties of the aortic wall. However, the mechanical properties of the aortic wall change as the aneurysm grows. For example, the collagen fibers in the aortic wall stiffen as the aortic aneurysm grows.

The mechanical properties of the aortic wall are remodeled at a series of discrete time stages to reflect the changes in the mechanical properties due to a progressively growing aortic aneurysm (block 220 of FIG. 2). In an advantageous embodiment, a parameter of the model representing the stiffness (or elasticity) of collagen fibers in the aortic wall can be modified to represent the changing (e.g., increasing) stiffness of the collagen fibers at each time stage.

At step 108, for each of the series of time stages, a stable deformation configuration of the aortic aneurysm is generated for the patient-specific aorta model. The stable deformation configuration for each time stage is generated by performing a Fluid Structure Interaction (FSI) simulation based on the re-modeled mechanical properties of the aortic wall at that time stage. The stable deformation configuration for each time stage provides an estimate the size of the aortic aneurysm at that time stage.

In one embodiment, fluid structure interaction (FSI) can be performed by coupling hemodynamics simulation to simulate the blood flow with the biomechanical simulation for the deformation of the aortic wall. The aorta is modeled as a passive tissue whose motion is governed by a constitutive law. A Finite Element Model (FEM) may be used to solve the partial differential equations related to that law. The wall motion of the aorta is driven by two forces:

1. An internal force that models the passive properties of the tissue. As an initial starting point, the aorta is modeled by a linear, isotropic, mono-layer elasticity model with co-rotational correction to cope with large deformations. In a second stage, a more detailed model can be utilized to simulate the heterogeneous composition of the artery (anisotropy, three main layers (tunica intima, tunica medica, and tunica adventitia), non-linearity, etc.).
2. An external force that models the loading generated by blood flow inside the structure. That loading, which translates into pressures, is applied to the inner layer of the structure.

Figure 3:
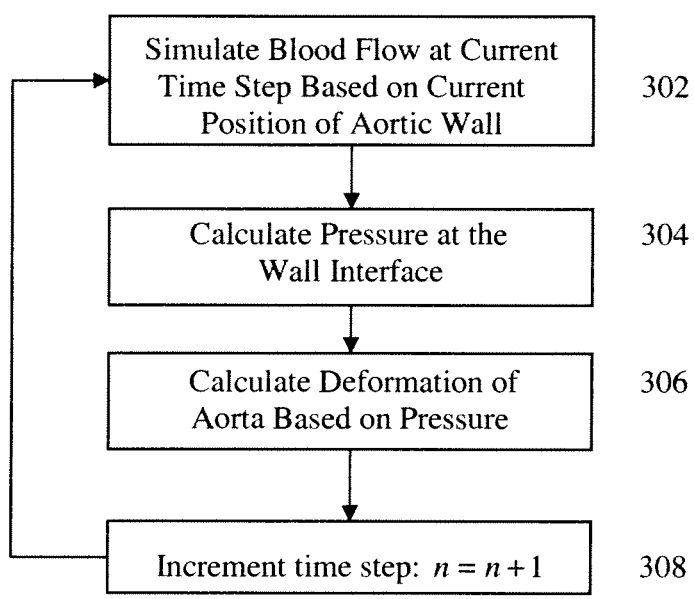
FIG. 3 illustrates an iterative method for estimating fluid structure interaction (FSI) of the aorta according to an embodiment of the present invention.

FIG. 3 illustrates an iterative method for estimating fluid structure interaction (FSI) of the aorta according to an embodiment of the present invention. The method of FIG. 3 can be used for each time stage to implement step 108 of FIG. 1. At step 302, the blood flow is simulated at a given time step based on a current position of the aortic wall. In an advantageous embodiment, the blood flow can be simulated based on the position of the aortic wall in the in the patient-specific 4D anatomical model at the current time step by solving Navier-Stokes equations constrained by the patient-specific 4D anatomical model using a level set framework, as described in U.S. patent application Ser. No. 13/091,076, entitled "Method and System for Comprehensive Patient-Specific Modeling of the Heart", filed Apr. 20, 2011, the disclosure of which is incorporated herein by reference. At step 304, the pressure at the wall interface is calculated at the current time step. It can be noted that the pressure at the blood/structure interface is calculated at each time step of the hemodynamics simulation. At step 306, a deformation is calculated for the aorta based on the pressure at the wall interface. The pressure acts as an external force on the wall of the aorta and causes the aorta to deform based on wall motion forces modeled for the aorta. At step 308, the time step increments (n=n+1), and the method returns to step 302. Accordingly, the calculated deformation of the aorta is used to simulate blood flow at the next time step. The method repeats until the end of the simulation. For example, the method may be repeated until a full heart cycle is simulated.

Figure 4:
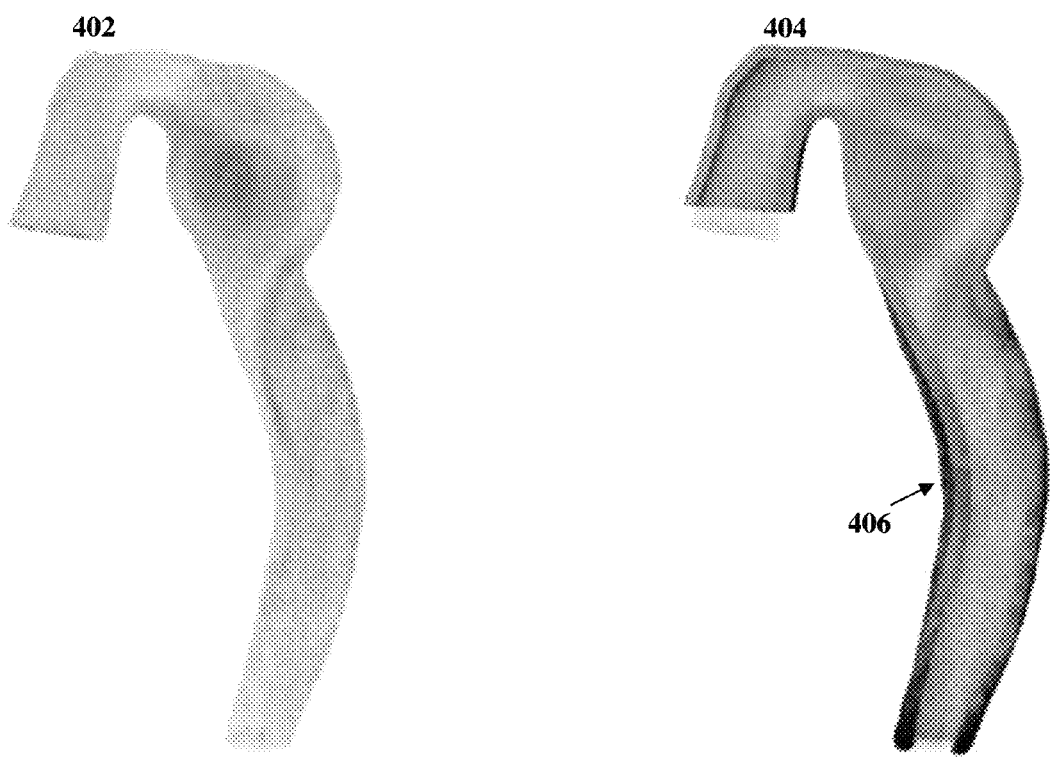
FIG. 4 illustrates exemplary results of estimating fluid structure interactions for the aorta.

FIG. 4 illustrates exemplary results of estimating fluid structure interactions for the aorta. Image 402 shows the blood flow simulation in the aorta at a particular time step. Image 404 shows the fluid structure interaction based on the blood flow simulation of image 404, which results in a deformed aortic wall 406.

The method of FIG. 3 can be performed for each time stage using the corresponding re-modeled mechanical properties of the aortic wall. This results in the stable deformation configuration for each time stage that is a 3D anatomical geometric model of the deformed aorta for that time stage. Referring to FIG. 2, block 230 illustrates exemplary stable deformation configuration results for three time stages. As shown in block 230, a stable deformation configurations 232, 234, and 236 are generated for time stages t1, t2, and t3, respectively.

Returning to FIG. 1, at step 110, virtual stent implantation is performed for each of the stable deformation configurations generated at step 108. Virtual stent implantation is the simulation of stent deployment at the aneurysm in the aorta. Block 240 of FIG. 2 illustrates virtual of stent deployment at an aneurysm in the aorta. As shown in block 240, a mesh 242 representing a stent is virtually implanted in the aorta 244 at an aneurysm. The force generated by the deployment of the stent deforms the aortic wall locally at the anchored sections of the stent. Fluid structure interactions are used to model this deformation. Modeling this deformation is crucial to assess the strength and the stent anchoring and its impact on the blood flow.

Figure 5:
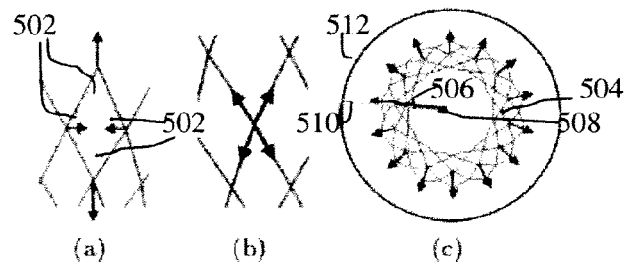
FIG. 5 illustrates forces acting on a stent mesh during virtual deployment.

Each stable deformation configuration is an anatomical model that includes the anatomy of aorta, including the aneurysm, at the corresponding time stage, which is used to perform an in-silico (virtual) delivery of the stent based on deformable simplex meshes and geometric constraints. The stent mesh can be a 2-simplex mesh that is used to guide the expansion of the stent in the virtual implantation. The expansion of the stent is modeled by balancing external and internal forces as encountered in the actual implantation procedure, using iterative approximation methods. The deformation of the device may be described by a finite discretization of a second order differential equation. FIG. 5 illustrates forces acting on the stent mesh during virtual deployment. As illustrated in FIG. 5, the arrows of image (a) represent the $f_{angle}$, which enforces characteristic angles 502 at the strut joints. The arrows of image (b) represent $f_{length}$, which maintains the strut lengths. Image (c) shows a short axis cross-section of the stent mesh. The arrows of image (c) represent $f_{circ}$, which enforces the circumference 504, while $f_{ext}$ dampens and eliminates all of the forces acting along the stent mesh normal weighted by a ratio of the distance 506 from the strut joint the stent centroid 508 and the distance 510 from the aortic wall 512 to the stent centroid 508. Based on the forces shown in FIG. 5, the implantation of the stent in the aortic aneurysm is simulated virtually. With such a framework, a different stent designs can be tested for each of the time stages in order to choose the optimal stent for the patient.

Returning to FIG. 1, at step 112, FSI simulations are performed for each virtual stent implantation. The FSI simulations can be performed by numerically solving the coupled fluid dynamics and solid mechanics equations for the blood flow and wall deformation, as described above in step 108. Referring to FIG. 2, block 250 illustrates exemplary results of FSI simulations in a stented aortic aneurysm.

At step 114, hemodynamic parameters for a functional assessment of the virtual stent implantation are determined based on the FSI simulations of step 112. The FSI simulations output simulated pressure and velocity for the blood flow in the stented aortic aneurysm. The simulated pressure and velocity can be used to determine various other hemodynamic parameters, such as wall shear stress, vorticity, etc. These parameters can be used to functionally assess the virtual stent implantation for treatment of the aortic aneurysm. This can be utilized for selecting a stent, determining a time for actual stent implantation, determining the optimal placement, and determining the effectiveness of stent implantation.

Figure 6:
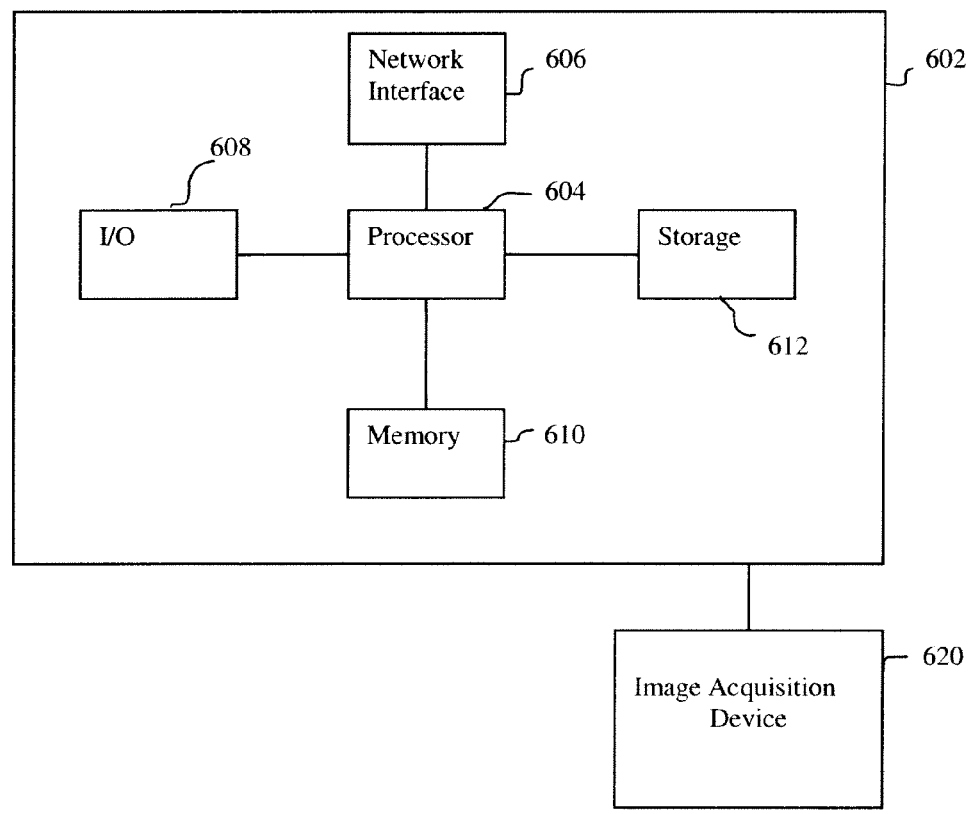
FIG. 6 is a high-level block diagram of a computer capable of implementing the present invention.

The above-described method for assessment of virtual stent implantation may be implemented on a computer using well-known computer processors, memory units, storage devices, computer software, and other components. A high-level block diagram of such a computer is illustrated in FIG. 6. Computer 602 contains a processor 604, which controls the overall operation of the computer 602 by executing computer program instructions which define such operation. The computer program instructions may be stored in a storage device 612 (e.g., magnetic disk) and loaded into memory 610 when execution of the computer program instructions is desired. Thus, the steps of the methods of FIGS. 1 and 3 may be defined by the computer program instructions stored in the memory 610 and/or storage 612 and controlled by the processor 604 executing the computer program instructions. An image acquisition device 620, such as a CT scanning device, MR scanning device, ultrasound device, etc., can be connected to the computer 602 to input image data to the computer 602. It is possible to implement the image acquisition device 620 and the computer 602 as one device. It is also possible that the image acquisition device 620 and the computer 602 communicate wirelessly through a network. The computer 602 also includes one or more network interfaces 606 for communicating with other devices via a network. The computer 602 also includes other input/output devices 608 that enable user interaction with the computer 602 (e.g., display, keyboard, mouse, speakers, buttons, etc.). Such input/output devices 608 may be used in conjunction with a set of computer programs as an annotation tool to annotate volumes received from the image acquisition device 620. One skilled in the art will recognize that an implementation of an actual computer could contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for assessment of virtual stent implantation in an aortic aneurysm, comprising:
   generating a patient-specific 4D anatomical model of the aorta from 4D medical imaging data;
   adjusting a model representing mechanical properties of the aorta wall to reflect changes to the mechanical properties of the aorta wall due to aneurysm growth at a plurality of time stages, resulting is respective re-modeled mechanical properties of the aorta wall at each of the plurality of time stages;
   generating a plurality of stable deformation configurations of the aorta, wherein each of the plurality of stable deformation configurations of the aorta is generated for a respective one of the plurality of time stages by performing a respective fluid structure interaction (FSI) simulation using the patient-specific 4D anatomical model at the respective one of the plurality time stages based on the respective re-modeled mechanical properties of the aorta wall at the respective one of the plurality of time stages;
   performing a respective virtual stent implantation for each of the plurality of stable deformation configurations of the aorta; and
   performing FSI simulations for each virtual stent implantation.

2. The method of claim 1, further comprising:
   determining at least one hemodynamic parameter for each virtual stent implantation based on results of the FSI simulations for each virtual stent implantation.

3. The method of claim 2, wherein the step of determining at least one hemodynamic parameter for each virtual stent implantation based on results of the FSI simulations for each virtual stent implantation comprises:
   determining at least one of wall shear stress and vorticity for each virtual stent implantation based on velocity and pressure values resulting from the FSI simulations for each virtual stent implantation.

4. The method of claim 1, wherein the step of generating a patient-specific 4D anatomical model of the aorta from 4D medical imaging data comprises:

generating an aorta mesh in each of a plurality of frames of the 4D medical imaging data using piece-wise aorta segmentation.

5. The method of claim 1, wherein the step of adjusting a model representing mechanical properties of the aorta wall to reflect changes to the mechanical properties of the aorta wall due to aneurysm growth at a plurality of time stages, resulting is respective re-modeled mechanical properties of the aorta wall at each of the plurality of time stages comprises:
characterizing the mechanical properties of the aorta wall using a mathematical model based on an underlying structural analysis of three layers of the aortic wall under internal pressure; and
adjusting at least one parameter of the mathematical model characterizing the mechanical properties of the aorta wall at each of the plurality of time stages to reflect changes in the at least one parameter due to a progressively growing aneurysm.

6. The method of claim 5, wherein the step of adjusting at least one parameter of the mathematical model characterizing the mechanical properties of the aorta wall at each of the plurality of time stages to reflect changes in the at least one parameter due to a progressively growing aneurysm comprises:
adjusting a parameter representing stiffness of collagen fibers in the aorta wall at each of the plurality of time stages.

7. The method of claim 1, wherein the step of generating a plurality of stable deformation configurations of the aorta, wherein each of the plurality of stable deformation configurations of the aorta is generated for a respective one of the plurality of time stages by performing a respective fluid structure interaction (FSI) simulation using the patient-specific 4D anatomical model at the respective one of the plurality time stages based on the respective re-modeled mechanical properties of the aorta wall at the respective one of the plurality of time stages comprises, for each of the plurality of time stages:
simulating blood flow in the patient-specific 4D anatomical model of the aorta at a current time step;
calculating a deformation of the aorta wall at the current time step based on the simulated blood flow at the current time step and the adjusted model representing the respective re-modeled mechanical properties of the aorta wall at the current time step; and
repeating the simulating and calculating steps for a plurality of time steps.

8. The method of claim 7, wherein the step of simulating blood flow in the patient-specific 4D anatomical model of the aorta at a current time step comprises:
simulating the blood flow in the patient-specific 4D anatomical model of the aorta by solving Navier-Stokes equations constrained by a geometry of the patient-specific 4D anatomical model of the aorta at the current time step using a level set framework.

9. The method of claim 7, wherein the step of simulating blood flow in the patient-specific 4D anatomical model of the aorta at a current time step comprises:
calculating pressure at a wall interface of the aorta at the current time step due to the simulated blood flow.

10. The method of claim 9, wherein the step of calculating a deformation of the aorta wall at the current time step based on the simulated blood flow at the current time step comprises:
calculating a deformation of the aorta wall due to the pressure at the wall interface of aorta.

11. The method of claim 1, wherein the step of performing a respective virtual stent implantation for each of the plurality of stable deformation configurations of the aorta comprises:
virtually simulating stent deployment at an aortic aneurysm in each of the plurality of stable deformation configurations of the aorta.

12. An apparatus for assessment of virtual stent implantation in an aortic aneurysm, comprising:
means for generating a patient-specific 4D anatomical model of the aorta from 4D medical imaging data;
means for adjusting a model representing mechanical properties of the aorta wall to reflect changes to the mechanical properties of the aorta wall due to aneurysm growth at a plurality of time stages, resulting is respective re-modeled mechanical properties of the aorta wall at each of the plurality of time stages;
means for generating a plurality of stable deformation configurations of the aorta, wherein each of the plurality of stable deformation configurations of the aorta is generated for a respective one of the plurality of time stages by performing a respective fluid structure interaction (FSI) simulation using the patient-specific 4D anatomical model at the respective one of the plurality time stages based on the respective re-modeled mechanical properties of the aorta wall at the respective one of the plurality of time stages;
means for performing a respective virtual stent implantation for each of the plurality of stable deformation configurations of the aorta; and
means for performing FSI simulations for each virtual stent implantation.

13. The apparatus of claim 12, further comprising:
means for determining at least one hemodynamic parameter for each virtual stent implantation based on results of the FSI simulations for each virtual stent implantation.

14. The apparatus of claim 13, wherein the means for determining at least one hemodynamic parameter for each virtual stent implantation based on results of the FSI simulations for each virtual stent implantation comprises:
means for determining at least one of wall shear stress and vorticity for each virtual stent implantation based on velocity and pressure values resulting from the FSI simulations for each virtual stent implantation.

15. The apparatus of claim 12, wherein the means for generating a patient-specific 4D anatomical model of the aorta from 4D medical imaging data comprises:
means for generating an aorta mesh in each of a plurality of frames of the 4D medical imaging data using piece-wise aorta segmentation.

16. The apparatus of claim 12, wherein the means for adjusting a model representing mechanical properties of the aorta wall to reflect changes to the mechanical properties of the aorta wall due to aneurysm growth at a plurality of time stages, resulting is respective re-modeled mechanical properties of the aorta wall at each of the plurality of time stages comprises:
means for characterizing the mechanical properties of the aorta wall using a mathematical model based on an underlying structural analysis of three layers of the aortic wall under internal pressure; and
means for adjusting at least one parameter of the mathematical model characterizing the mechanical properties of the aorta wall at each of the plurality of time stages to reflect changes in the at least one parameter due to a progressively growing aneurysm.

17. The apparatus of claim 16, wherein the means for adjusting at least one parameter of the mathematical model characterizing the mechanical properties of the aorta wall at each of the plurality of time stages to reflect changes in the at least one parameter due to a progressively growing aneurysm comprises:
 means for adjusting a parameter representing stiffness of collagen fibers in the aorta wall at each of the plurality of time stages.

18. The apparatus of claim 12, wherein the means for generating a plurality of stable deformation configurations of the aorta, wherein each of the plurality of stable deformation configurations of the aorta is generated for a respective one of the plurality of time stages by performing a respective fluid structure interaction (FSI) simulation using the patient-specific 4D anatomical model at the respective one of the plurality time stages based on the respective re-modeled mechanical properties of the aorta wall at the respective one of the plurality of time stages comprises:
 means for simulating blood flow in the patient-specific 4D anatomical model of the aorta at a current time step; and
 means for calculating a deformation of the aorta wall at the current time step based on the simulated blood flow at the current time step and the adjusted model representing the mechanical properties of the aorta wall.

19. The apparatus of claim 12, wherein the means for performing a respective virtual stent implantation for each of the plurality of stable deformation configurations of the aorta comprises:
 means for virtually simulating stent deployment at an aortic aneurysm in each of the plurality of stable deformation configurations of the aorta.

20. A non-transitory computer readable medium encoded with computer executable instructions for assessment of virtual stent implantation in an aortic aneurysm, the computer executable instructions defining steps comprising:
 generating a patient-specific 4D anatomical model of the aorta from 4D medical imaging data;
 adjusting a model representing mechanical properties of the aorta wall to reflect changes to the mechanical properties of the aorta wall due to aneurysm growth at a plurality of time stages, resulting is respective re-modeled mechanical properties of the aorta wall at each of the plurality of time stages;
 generating a plurality of stable deformation configurations of the aorta, wherein each of the plurality of stable deformation configurations of the aorta is generated for a respective one of the plurality of time stages by performing a respective fluid structure interaction (FSI) simulation using the patient-specific 4D anatomical model at the respective one of the plurality time stages based on the respective re-modeled mechanical properties of the aorta wall at the respective one of the plurality of time stages;
 performing a respective virtual stent implantation for each of the plurality of stable deformation configurations of the aorta; and
 performing FSI simulations for each virtual stent implantation.

21. The non-transitory computer readable medium of claim 20, further comprising computer executable instructions defining the step of:
 determining at least one hemodynamic parameter for each virtual stent implantation based on results of the FSI simulations for each virtual stent implantation.

22. The non-transitory computer readable medium of claim 21, wherein the computer executable instructions defining the step of determining at least one hemodynamic parameter for each virtual stent implantation based on results of the FSI simulations for each virtual stent implantation comprise computer executable instructions defining the step of:
 determining at least one of wall shear stress and vorticity for each virtual stent implantation based on velocity and pressure values resulting from the FSI simulations for each virtual stent implantation.

23. The non-transitory computer readable medium of claim 20, wherein the computer executable instructions defining the step of generating a patient-specific 4D anatomical model of the aorta from 4D medical imaging data comprise computer executable instructions defining the step of:
 generating an aorta mesh in each of a plurality of frames of the 4D medical imaging data using piece-wise aorta segmentation.

24. The non-transitory computer readable medium of claim 20, wherein the computer executable instructions defining the step of adjusting a model representing mechanical properties of the aorta wall to reflect changes to the mechanical properties of the aorta wall due to aneurysm growth at a plurality of time stages, resulting is respective re-modeled mechanical properties of the aorta wall at each of the plurality of time stages comprise computer executable instructions defining the steps of:
 characterizing the mechanical properties of the aorta wall using a mathematical model based on an underlying structural analysis of three layers of the aortic wall under internal pressure; and
 adjusting at least one parameter of the mathematical model characterizing the mechanical properties of the aorta wall at each of the plurality of time stages to reflect changes in the at least one parameter due to a progressively growing aneurysm.

25. The non-transitory computer readable medium of claim 24, wherein the computer executable instructions defining the step of adjusting at least one parameter of the mathematical model characterizing the mechanical properties of the aorta wall at each of the plurality of time stages to reflect changes in the at least one parameter due to a progressively growing aneurysm comprise computer executable instructions defining the step of:
 adjusting a parameter representing stiffness of collagen fibers in the aorta wall at each of the plurality of time stages.

26. The non-transitory computer readable medium of claim 20, wherein the computer executable instructions defining the step of generating a plurality of stable deformation configurations of the aorta, wherein each of the plurality of stable deformation configurations of the aorta is generated for a respective one of the plurality of time stages by performing a respective fluid structure interaction (FSI) simulation using the patient-specific 4D anatomical model at the respective one of the plurality time stages based on the respective re-modeled mechanical properties of the aorta wall at the respective one of the plurality of time stages comprise computer executable instructions defining the steps of, for each of the plurality of time stages:
 simulating blood flow in the patient-specific 4D anatomical model of the aorta at a current time step;
 calculating a deformation of the aorta wall at the current time step based on the simulated blood flow at the current time step and the adjusted model representing the respective re-modeled mechanical properties of the aorta wall at the current time step; and
 repeating the simulating and calculating steps for a plurality of time steps.

27. The non-transitory computer readable medium of claim 20, wherein the computer executable instructions defining the step of performing a respective virtual stent implantation for each of the plurality of stable deformation configurations of the aorta comprise computer executable instructions defining the step of:

virtually simulating stent deployment at an aortic aneurysm in each of the plurality of stable deformation configurations of the aorta.

* * * * *